United States Patent [19]
Day

[11] Patent Number: 5,947,735
[45] Date of Patent: Sep. 7, 1999

[54] SURFACE ROUGHENING OF SELF-TAPPING DENTAL IMPLANTS

[75] Inventor: Thomas H. Day, San Diego, Calif.

[73] Assignee: Sulzer Calcitek Inc., Carlsbad, Calif.

[21] Appl. No.: 08/966,627

[22] Filed: Nov. 10, 1997

[51] Int. Cl.⁶ .................................................. A61C 8/00
[52] U.S. Cl. ......................................... 433/173; 433/174
[58] Field of Search ................................. 433/172, 173, 433/174, 175, 176

[56] References Cited

U.S. PATENT DOCUMENTS

| | | | |
|---|---|---|---|
| 5,195,891 | 3/1993 | Sulc | 433/174 X |
| 5,324,199 | 6/1994 | Branemark | 433/174 |
| 5,344,457 | 9/1994 | Pilliar et al. | 433/174 X |
| 5,588,838 | 12/1996 | Hansson et al. | 433/174 X |
| 5,591,029 | 1/1997 | Zuest | 433/174 X |
| 5,639,237 | 6/1997 | Fontenot | 433/174 X |

*Primary Examiner*—Nicholas D. Lucchesi
*Attorney, Agent, or Firm*—Philip S. Lyren

[57] ABSTRACT

A self-tapping dental implant includes a body which is substantially covered by a random surface roughening without adversely affecting the cutting edge and thus the amount of torque needed to thread the implant into bone tissue. During the surface treatment process, the cutting edges of the implant are covered with a removable shield. The shield may engage the implant through openings on either side of the cutting edge. The shield is adaptable for use with implants having multiple cutting edges since the shield may include a plurality of arms connected by a base. The shield may be snapped onto the distal end of the implant.

21 Claims, 1 Drawing Sheet

SURFACE ROUGHENING OF SELF-TAPPING DENTAL IMPLANTS

BACKGROUND OF THE INVENTION

This invention relates generally to self-tapping dental implants and particularly to techniques for forming roughened surfaces on self-tapping dental implants.

Dental implants are used to provide a tooth-like structure in areas where both the tooth and the root are missing. Areas where all tooth structure is absent, called edentulous regions, may exist where one or more teeth have been lost.

A typical dental implant has a generally cylindrical structure. The cylindrical body of the implant is secured into the jawbone with the upper proximal edge or neck portion located at or above the jawbone crest. The neck portion often has a threaded bore for receiving an abutment that mounts the artificial tooth. The opposite end of the implant, called the distal end, is located in a position anchored within the jawbone.

By a process known as osseointegration, the implant becomes integrally bonded with the bone tissue over time. In this way the implant may be very securely retained in the jaw structure.

Self-tapping implants include at least one longitudinal cutting groove extending along the length of the implant body. Usually the cutting groove extends a substantial portion of the length of the implant down to its distal end. Two or more cutting grooves may be circumferentially spaced about the implant.

As the implant body is rotated into the bone structure, the cutting groove scrapes away bone tissue like a tap. These bone tissue fragments may be secured inside implant body openings adjacent the groove. Further, the bone fragments may re-grow to form bone that is interengaged with the implant.

Self-tapping dental implants have many advantages. One important advantage is that the implantologist is able to save time during the implantation process. Since the implant simultaneously taps the bone during insertion, a separate tapping stage is not necessary. This time saving results in economies as well as decreased air exposure to the exposed implantation site and, therefore, decreased likelihood of infection. In addition, self-tapping implants may have better stability and more intimate contact with the bone. Thus, self-tapping implants may achieve better osseointegration *inter alia* because of the bone fragments formed in the cutting process and the enhanced opportunity for the growth of new bone tissue.

Self-tapping implants should have relatively sharp cutting edges to avoid the necessity for very high insertion torque during installation. Greater insertion torque during insertion can damage the engaging neck portion at the proximal end of the implant. In addition, the need for high torque may result in an implant that is not fully seated in the bone tissue. Also, the need for high torque may increase the installation time.

Random surface roughness in dental implants, in general, increases the stability and osseointegration of those implants. One theory is that the roughened surface provides spacing between the implant and the bone surface where osseointegration may occur. While it is possible to machine roughened features onto the dental implant surface, random roughness may be more effective in achieving osseointegration.

One explanation for the integration that occurs due to surface roughening is that osteoblast-like cells cover the implant surface to integrate the bone. These cells are apparently able to attach themselves to the implant surface better when that surface is rough. Generally the micromorphologic characteristics of the surface determine the response of these cells to the implant.

Random surface roughness may result from either subtractive or additive processes. An example of a subtractive process is particle bombardment of the surface. Particle bombardment processes include grit blasting with titanium oxide or aluminum oxide. The amount of roughness achieved may be different depending on the particle size, force and duration. Another subtractive process is acid etching the surface, for example, using hydrofluoric acid. Similarly, ion etching, chemical milling, laser etching, and spark erosion may have applicability in dental implant surface roughening.

Additive processes may result in the build up of rough textured surface features on dental implants. Examples of additive processes include the molten titanium plasma spray or "TPS" process and the HA coating process. Generally, bone compatible bioreactive materials such as apatite materials can be used to form an HA coating on the implant surface. Examples of useful apatite materials include hydroxyapatite and whitlocktite.

The HA coatings may be high crystallinity, creating a roughness approximating that achieved with acid etching. Lower density or lower crystallinity HA coatings can match or exceed the roughness achieved through TPS or grit blasting.

The application of random surface roughening techniques to self-tapping implants raises an important issue. While surface roughening, like the self-tapping implant technology, aids in osseointegration, surface roughening, dulls the cutting edge or surface. In turn, this dulled edge increases the friction between the implant and the bone during installation. As a result, the necessary installation torque is increased, giving rise to the possibility of the problems attendant to increased torque, discussed above.

It would be very desirable to have a technique which enables self-tapping implants to be surface roughened without the need for increased insertion torques. Such techniques could enable the advantages of both the self-tapping technology and the random surface roughness technology to be achieved in a single implant.

Some self-tapping implants roughen a middle portion of the body and leave the entire distal end relatively unroughened. These implants maintain a sharp cutting edge. But, the benefits of roughening are not fully achieved on the implant body since a significant portion of the submerged implant is not roughened. An implant that had a roughened distal portion yet maintained a sharp cutting edge would be advantageous.

SUMMARY OF THE INVENTION

In accordance with one aspect of the present invention, a self-tapping dental implant includes a generally cylindrical body. At least one cutting edge extends over at least a portion of the body. The body includes a roughened surface region. The cutting edge however is substantially free of roughening.

In accordance with another aspect, a method for surface roughening is provided for a self-tapping dental implant that has cylindrical body with at least one cutting edge extending over the body. The method may include the step of exposing a substantial portion of the body to a roughening treatment. The cutting edge is shielded from the treatment and thus does not become dull.

In accordance with yet another aspect of the present invention, a shield is provided for a self-tapping dental implant with a generally cylindrical body and at least one cutting edge extending over the body. The shield includes a first portion adapted to extend over the cutting edge when the cutting edge is exposed to a surface roughening treatment. The second portion is adapted to releasably secure the first portion to the dental implant.

One of the advantages of the present invention, include the possibility of achieving the effects of surface roughening in self-tapping implants without the need for increased insertion torque. In addition, in some instances, it may be possible to increase the potential area exposed to surface roughening without adverse effects on the cutting edge and hence on the insertion torque. Increased roughened surface area may also advantageously increase the force necessary to remove the implant once it is implanted.

The details of one or more embodiments of the invention are set forth in the accompanying drawings and the description below. Other features, objects and advantages will be apparent from the description and drawings, and from the claims.

DESCRIPTION OF THE PREFERRED EMBODIMENTS

Figure 1:
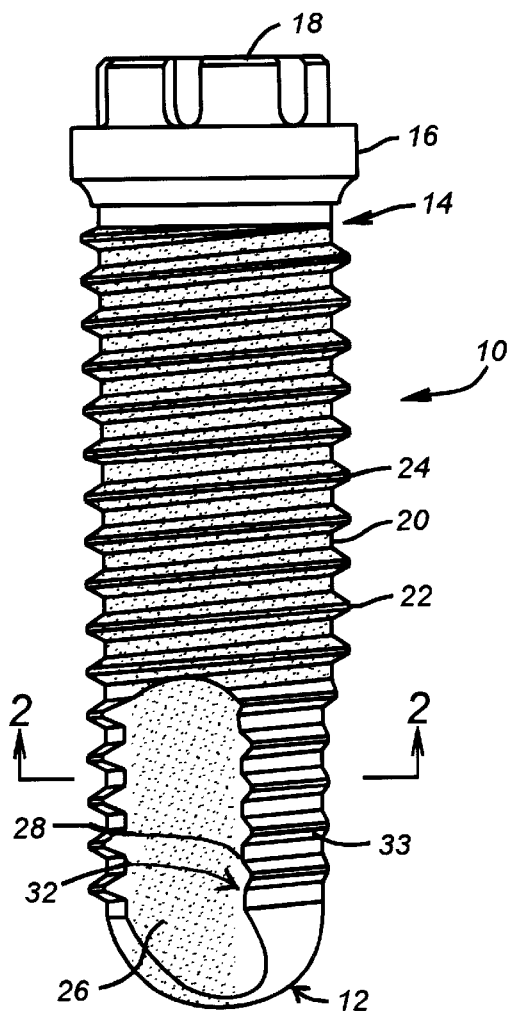
FIG. 1 is a front elevational view of one embodiment of the present invention.

Referring to the drawing wherein like reference characters are utilized for like parts throughout the several views, a self-tapping dental implant 10, shown in FIG. 1, includes a distal end 12 and a proximal end 14. Adjacent to the proximal end 14 is a neck portion 16 which may be unroughened. In one particular embodiment, the neck portion 16 includes an anti-rotational feature such as a plurality of splines 18 which prevent relative rotation with respect to an abutment coping, or other prosthetic component (not shown) secured to the neck portion 16. Of course, the use of the anti-rotational feature is completely optional and other non-rotational structures known in the art may be used as well.

The body 20 of the implant 10 may be generally cylindrical with a slight proximal to distal taper. The distal end 12 may be slightly smaller in diameter than the portion of the body 20 adjacent the proximal end 14. The body 20 has a screw thread 22 formed on its surface. While the illustrated screw thread 22 includes a blunt edge 24, other configurations of the thread known in the art may be used as well.

The distal end 12 of the implant 10 includes one or more cutting edges or surfaces defining openings 26. The number of openings 26 may be varied, but commonly two or more openings 26 are used. The openings 26 may extend completely through the implant 10 or they may be formed as cavities defining depressions in the surface of the implant body. One exposed edge or surface along the opening 26 defines a longitudinal cutting edge 28. The cutting edge 28 scrapes bone fragments from the surrounding bone tissue as the gently tapering implant extends into the bone structure and rotation is applied to the neck portion 16. In the illustrated embodiment, with three openings 26, three cutting edges 28 extend longitudinally at approximately 120 degrees from one another.

A concave cutting surface 32 is defined in conjunction with each cutting edge 28. In addition, each cutting edge 28 is bounded on one side by a convex surface 33.

Substantially the entire surface of the body 20 is exposed to one or more random surface roughening treatments. The useful treatments include any known subtractive treatment, additive treatment (including those described above), or any other treatment known in the art. In addition, as mentioned earlier, it is possible to follow a subtractive treatment with an additive treatment to achieve a desired degree of roughness. Generally, it is desirable to maximize the percentage of the body 20 in contact with bone tissue that is roughened. Maximizing the roughened area on the body aids osseointegration and increases the removal torque of the implant.

Referring to FIG. 1, a substantial portion of the surface of the body 20 is roughened while the concave surfaces 32, including to the cutting edges 28, are substantially unroughened. "Substantially unroughened" indicates that a region, as for example region 33, has not been exposed to the same extent of deliberate roughening processes. In some specific applications it may be desirable to slightly roughen the concave surfaces 32 but generally the surface 33 has little or no roughening. At the same time, the cutting edge and the neck portion preferably have absolutely no roughening.

By eliminating the roughening about the cutting edges 28, the ability of the cutting edges 28 to cut the bone tissue is substantially unaffected by the roughening process. As a result, it is possible to use a self-tapping implant having the advantages of surface roughening without suffering the concomitant disadvantage of requiring increased installation torque.

Figure 2:
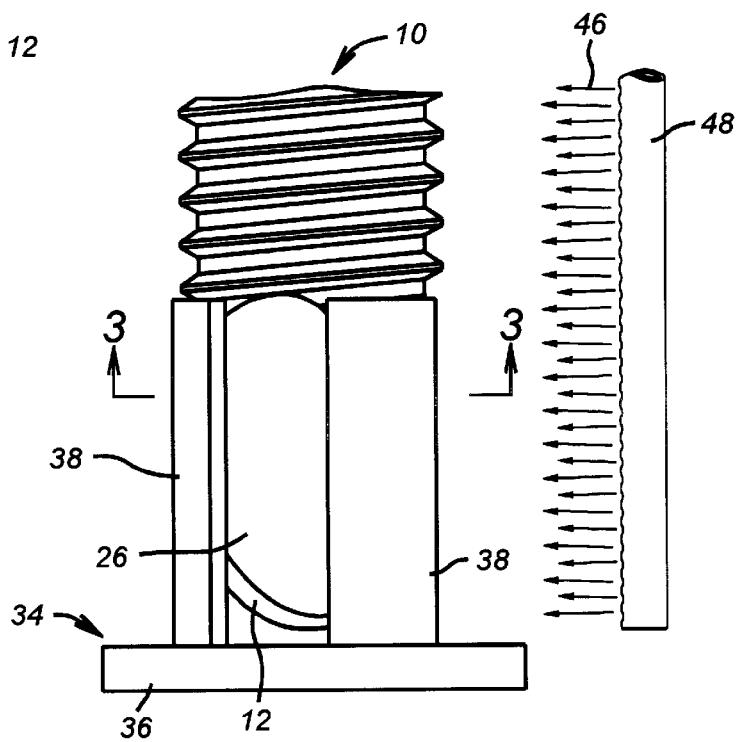
FIG. 2 is a partial front elevational view of the embodiment in FIG. I shown in the process of being exposed to a surface roughening treatment.

Referring to FIG. 2, a removable shield 34 is shown in position on the distal end 12 of the implant 10. The shield 34 generally covers the cutting edges 28 of the implant 10. The shield 34 may include a base 36 which connects with a plurality of longitudinally extending arms 38. In the illustrated embodiment, the arms 38 frictionally and releasably secure to the cutting edges 28.

Figure 3:
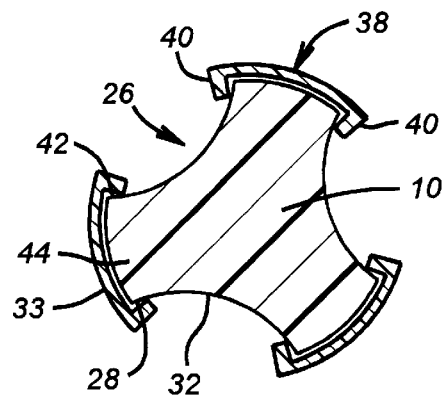
FIG. 3 is an enlarged cross-sectional view taken generally along the line 3—3 in FIG. 2.

More particularly, referring to FIG. 3, each arm 38 may include a pair of fingers 40 that may be resiliently biased against the cutting edge 28 and the opposed non-cutting edge 42. Those fingers 40 secure the arm 38 in a position to completely protect the cutting edge 28. In this way, the arms 38 may resiliently snap fit onto the portion 44 defined between adjacent openings 26. However those skilled in the art will appreciate a number of different ways that the arms 38 may be secured releasably to the portions 44.

Referring again to FIG. 2, with the shield 34 in position, the dental implant 10 can be exposed to a surface roughening technique. In particular, the implant 10 may be exposed to a spray 46 from an applicator 48. The applicator 48 may be one which implements a subtractive process, such as grit blasting or sandblasting, or may also be one which applies an additive process such as an HA coating or TPS process.

Because of the imposition of the shield 34, a substantial surface area of the implant 10 may be roughened without degrading the performance of the cutting edge 28 due to surface roughening. The shield 34 may be made in one or more pieces, for example by plastic molding. Advantageously, the arms 38 are formed of a resilient material.

While the present invention has been described with respect to a single embodiment, those skilled in the art will appreciate numerous modifications and variations therefrom. For example, it may be desirable to have the arms 38 open so as to expose more of the portion 44 between the openings 26 as well as the non-cutting edge 42 to the roughening treatment. In addition, with spiraled cutting edges the arms 38 may be similarly spiraled to follow the contours of the cutting edges. Also it may be advantageous to include an inward facing tab on each of the free ends of the fingers 40 to help to releasably lock the shield over the portions 44. It is intended that the appended claims cover all such modifications and variations as fall within the true spirit and scope of the present invention.

What is claimed is:

1. A self-tapping dental implant comprising: a generally cylindrical body;

two cutting edges extending over said body with a substantially roughened region between said two cutting edges; and said cutting edges being substantially free of roughening.

2. The implant of claim 1 wherein said generally cylindrical body includes a neck portion that is substantially free of roughening.

3. The implant of claim 1 including a plurality of cutting edges extending longitudinally along said cylindrical body, each of said cutting edges being spaced substantially equally from an adjacent cutting edge and being substantially free of roughening.

4. The implant of claim 1 wherein said body includes a neck portion; and said neck portion and said cutting edges are substantially unroughened and the rest of said body is roughened.

5. The implant of claim 1 wherein said cutting edges, a neck portion located at a proximal end, and a region adjacent said cutting edge are free of roughening and the remainder of the implant is substantially covered by roughening.

6. The implant of claim 5 wherein said roughening includes additive roughening.

7. The implant of claim 5 wherein said roughening includes subtractive roughening.

8. The implant of claim 5 wherein said roughening includes both subtractive and additive roughening.

9. A method for surface roughening a self-tapping dental implant having a cylindrical body with at least one cutting edge extending over said body, said method comprising the steps of:

exposing a substantial portion of said body to a roughening treatment; and shielding the cutting edge of said body from said treatment.

10. The method of claim 9 including the step of releasably securing a shield member over the cutting edge of said body prior to said roughening treatment.

11. The method of claim 9 including the step of exposing said body to a subtractive roughening treatment.

12. The method of claim 9 including the step of exposing said body to an additive roughening treatment.

13. The method of claim 9 including the step of exposing said body to both a subtractive and an additive roughening treatment.

14. The method of claim 9 including the step of shielding said cutting edge from all roughening treatments.

15. The method of claim 9 including the step of resiliently securing a shield over said cutting edge.

16. The method of claim 15 including the step of securing a shield simultaneously over a plurality of cutting edges on a single implant.

17. The method of claim 9 including the step of resiliently securing said shield over a portion of said body between two adjacent openings by securing said shield from one opening to the adjacent opening.

18. The method of claim 9 wherein said shielding step includes the step of releasably securing a shield onto at least one cutting edge.

19. A self-tapping dental implant, comprising:

a generally cylindrical body with a neck portion at a proximal end;

two cutting edges extending over a portion of said body;

two cavities adjacent said cutting edges; and said body and said cavities being substantially roughened with said cutting edges and said neck portion being substantially unroughened.

20. The self-tapping dental implant of claim 19 in which:

said cutting edges and said cavities extend from a distal end of said body upwardly toward said neck portion;

said body further includes a convex surface adjacent said cavities; and said convex surface being substantially unroughened.

21. The self-tapping dental implant of claim 20 in which said cavities define depressions in said body.

* * * * *